(12) United States Patent
Liu et al.

(10) Patent No.: US 11,666,406 B2
(45) Date of Patent: Jun. 6, 2023

(54) METHOD FOR GENERATING FORCE FEEDBACK OF REMOTE SURGICAL DEVICE

(71) Applicants: GAMANIA DIGITAL ENTERTAINMENT CO., LTD., Taipei (TW); CATHAY GENERAL HOSPITAL, Taipei (TW)

(72) Inventors: Po-Yun Liu, Taipei (TW); Hsien-Che Chuang, Taipei (TW); Chih-Cheng Chien, Taipei (TW); Yen-Chieh Wang, Taipei (TW)

(73) Assignee: Gamania Digital Entertainment, Co., Ltd., Taipei (TW)

( * ) Notice: Subject to any disclaimer, the term of this patent is extended or adjusted under 35 U.S.C. 154(b) by 0 days.

(21) Appl. No.: 17/481,665

(22) Filed: Sep. 22, 2021

(65) Prior Publication Data
US 2023/0036677 A1    Feb. 2, 2023

(51) Int. Cl.
| | |
|---|---|
| *A61B 34/35* | (2016.01) |
| *A61B 34/00* | (2016.01) |
| *G06F 3/01* | (2006.01) |
| *A61B 90/00* | (2016.01) |
| *G06T 7/194* | (2017.01) |
| *G06V 10/25* | (2022.01) |
| *G06V 10/56* | (2022.01) |
| *G06V 20/20* | (2022.01) |

(52) U.S. Cl.
CPC ............ *A61B 34/76* (2016.02); *A61B 34/35* (2016.02); *A61B 90/37* (2016.02); *G06F 3/016* (2013.01); *G06T 7/194* (2017.01); *G06V 10/25* (2022.01); *G06V 10/56* (2022.01); *G06V 20/20* (2022.01); *A61B 2090/066* (2016.02); *G06F 2203/014* (2013.01)

(58) Field of Classification Search
CPC ......... A61B 34/76; A61B 34/35; A61B 90/37; A61B 2090/066; A61B 34/30; G06T 7/194; G06V 10/25; G06V 20/20; G06V 10/56; G06F 3/016; G06F 2203/014
See application file for complete search history.

(56) References Cited

U.S. PATENT DOCUMENTS

2018/0338806 A1* 11/2018 Grubbs ................. A61B 34/30

\* cited by examiner

*Primary Examiner* — Abdul-Samad A Adediran
(74) *Attorney, Agent, or Firm* — Rosenberg, Klein & Lee

(57) ABSTRACT

The present invention is a method for controlling a Davinci surgical device. Firstly, controlling an operation part of a remote operation device to enter the inner of a body for executing a surgical operation. Then, an image capturing unit captures a plurality of corresponding surgical images to a control device, and the control device obtains a first torque component, a second torque component and an element action of the remote surgical device according to the surgical images to operate an output strength of the remote surgical device for further generating corresponding strength feedback by the output strength. Thus, the user can get the control status of the remote surgical device to prevent accidental iatrogenic injury from over-force and to proceed with the operation with improved accuracy.

11 Claims, 11 Drawing Sheets

METHOD FOR GENERATING FORCE FEEDBACK OF REMOTE SURGICAL DEVICE

FIELD OF THE INVENTION

This application relates to a method for generating force feedback, particularly a method for generating a force feedback from a remote surgical device.

BACKGROUND OF THE INVENTION

Nowadays, with the vigorous development of mechanism, automatic control and computer technology, robotic arms provide high-efficiency and stable automatic control, particularly for remote operation.

Generally speaking, a remote surgical device is that a surgical surgeon operates a remote surgical device to perform a surgical operation, such as a Davinci surgical robot. The remote surgical device generally uses a robotic arm to perform surgical operations.

Although the remote surgical device provides a minimally invasive and stable operation through semi-automatic control, yet, the robotic arms for performing surgical operations do not allow the operator to easily realize the control status of the surgical devices through having the hand-held surgical instruments touch the organs and tissues of the anatomical part to be repaired or removed as the proximal surgical operation does; there are unknowable force-taking or torque-taking condition exerted to the robotic arm while the remote surgical device operator is using a robotic arm to perform a remote surgical operation, which would make the operator of a robotic arm unable to make an immediate response when an accident occurs, and that would cause the damage issue.

To solve the issue of unpredictable damage due to the reason of unable to realize the force-taking or torque-taking condition of the robotic arm, some vendors have developed a force feedback glove, which is externally added to the original robotic arm. Yet, for surgical devices, each additional device means an additional cost. In addition, the remote surgical device is more precise in the control of the robotic arm, so it is also necessary to pay attention to the cost of the equipment.

According to the aforesaid issue, this application provides a method of using a remote surgical device to generate the force feedback, which can perform the surgical operation and analyze the first and second torque components and the element action of the remote surgical device at the same time, obtaining the output strength of the remote surgical device during the surgical operation; except avoiding iatrogenic injuries made from excessive torques exerted to the remote surgical device, it can perform a more accurate surgical operation.

SUMMARY

One objective of this application is to provide a method of generating force feedback from a remote surgical device; using operation image taken in a surgical operation, it can perform the surgical operation and analyze the torques and element action of the remote surgical device and obtains the output strength of the remote surgical device required during the surgical operation. This method not only can avoid iatrogenic injuries from excessive torques exerted to the remote surgical device, but also can perform a more accurate surgical operation.

For achieving the aforesaid objective, this application provides a method of generating force feedback using a remote surgical device. First, this method uses an image capturing unit of a remote surgical device to capture a plurality of surgical operation images to a control device; next, the control device follows the surgical operation images to obtain a first torque component of the operating portion; and the control device following the first torque component and a second torque component exerted to the operating portion of the remote surgical device to operate an output strength of the remote surgical device; through the output strength, it further generates a force feedback. From this process, it can have the control device generate the force feedback toward the surgical operating movements of the remote surgical device; except avoiding iatrogenic injuries made from excessive torques exerted to the remote surgical device, it can perform a more accurate surgical operation.

This application provides an embodiment, wherein in the step of using an image capturing unit in the remote surgical device to capture a plurality of corresponded surgical operating images to a control device, it further uses a pressure sensor to detect a pressure taken by the operating portion.

This application provides an embodiment, wherein in the step that the control device follows the first torque component and a second torque component from the remote surgical device to the operating portion to operate an output strength of the remote surgical device, the control device further follows the pressure taken by the remote surgical device to operate the output strength.

This application provides an embodiment, wherein the operating portion is connected with a jig, a drill, a file, a scraper, a saw, a screwdriver, or a surgical tool for repairing or removing part of the tissue by drilling, grinding, cutting, or scraping. The operating portion is equipped with a pressure sensor, a piezoelectric sensor, an elastic sensor, an optical camera, a laser scanner or an ultrasonic scanner.

This application provides an embodiment, wherein in the step that the control device follows the surgical operation images to obtain a first torque component of the operating portion, it cuts the operation images into a plurality of image zones, and follows a matching algorithm to analyze the image zones to obtain a plurality of movement images for the remote surgical device; next, follow the movement images to obtain a plurality of foreground images and at least one background image, and then compare the foreground images and the background image to obtain the first torque component.

This application provides an embodiment, wherein in the step of obtaining a plurality of movement images of the remote surgical device, it further labels these movement images.

This application provides an embodiment, wherein in the step that follows the movement images to obtain a plurality of foreground images and at least a background image, it further follows a plurality of element center points in the foreground images to get an output strength vector and uses the vector to obtain the first torque component.

This application provides an embodiment, wherein in the step that compares the foreground images and the background image, it further obtains a color of the background image and uses the color to compare a color coefficient table used to adjust the first torque component.

This application provides an embodiment, wherein the matching algorithm is the Full search, Three-step search, Diamond search, Sum of absolute difference (SAD), Mean absolute error (MAE) or Mean squared error (MSE).

This application provides an embodiment, wherein in the step that the control device follows the output strength to generate a force feedback, the control device follows the output strength to generate an image or a mechanical operation corresponding to the force feedback.

This application provides an embodiment, wherein the displayed image is a numerical image of strength and the mechanical operation is a feedback thrust.

DETAILED DESCRIPTION

The well-known control method of remote surgical devices is to directly refer to the images and operate directly; this application has changed the defects of the well-known control method on the remote surgical device. Except for avoiding the occurrence of unexpected iatrogenic injury made from excessive force, the operation can be performed more accurately, and damages to the equipment can also be avoided.

In the statement below, various embodiments of this application are to be described in detail using graphics. However, the concept of this application can be embodied in many different forms and should not be interpreted as limiting to the exemplary embodiments described herein.

Figure 1:
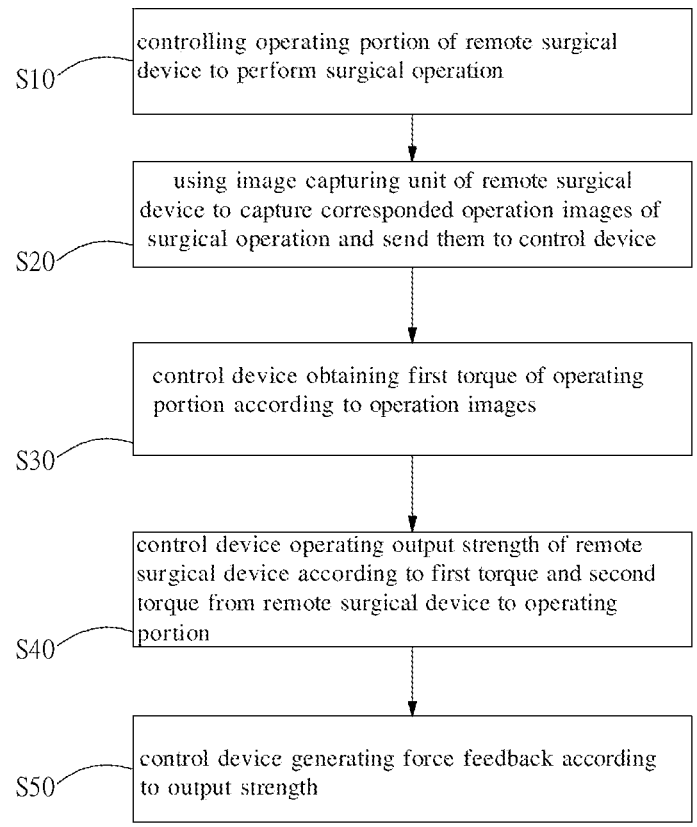
FIG. 1: Flowchart in an embodiment of this application.

The operating flow of the method that the remote surgical device generates the force feedback is shown in FIG. 1, which is an embodiment of this application; as shown in FIG. 1, the steps are as follows:

Step S10: controlling operating portion of remote surgical device to perform surgical operation;

Step S20: using image capturing unit of remote surgical device to capture corresponded operation images of surgical operation and send them to control device;

Step S30: control device obtaining first torque component of operating portion according to operation images;

Step S40: control device operating output strength of remote surgical device according to first torque component and second torque component from remote surgical device to operating portion; and Step S50: control device generating force feedback according to output strength.

The operating step flows of the remote surgical device in this application are shown in steps S10 to step S40. To explain the operating step flow of the remote surgical device generating the force feedback in this application in a more specific way, an actual example is made as follow description; please refer to FIG. 2A to FIG. 2E, which are the schematic diagrams of devices in an embodiment of this application. As shown in the figures, the surgical operation system 1 of this application includes a Control Device 10 and a Remote Surgical Device 20; the embodiment shows that the Control Device 10 is connected with the Remote Surgical Device 20 via the transmission cable; yet, it isn't limited to this arrangement in this application; the Control Device 10 can also transmit the control signals to the Remote Surgical Device 20 via wireless way. The Remote Surgical Device 20 is equipped with at least an Operating Portion 22; in this embodiment, the Remote Surgical Device 20 is equipped with a Seat 22 and a plurality of Operating Portion 24; these Operating Portion 24 are connected with an Image Capturing Unit C, a First Surgical Tool ST1, a Second Surgical Tool ST2 and a Third Surgical Tool ST3; the First Surgical Tool ST1 is connected with a Mini Scalpel ST11; the Second Surgical Tool ST2 is connected with a Jig ST21, and the Third Surgical Tool ST3 is connected with a Drill ST31. The Operating Portion 24 is the robotic arm; the Control Device 10 transmits the control order CTRL to the Remote Surgical Device 20. Except that the Operating Portion 24 is connected with the Mini Scalpel ST11, the Jig ST21, and the Drill ST31, the Mini Scalpel ST11 can be a file, a scraper, a saw, a screwdriver, or a surgical tool for repairing or removing part of the tissue by drilling, grinding, cutting or scraping. Moreover, the Operating Portion 24 can further be equipped with a Sensor 26, which is a pressure sensor, a piezoelectric sensor, an elastic sensor, an optical camera, a laser scanner or an ultrasonic scanner.

Figure 2A:
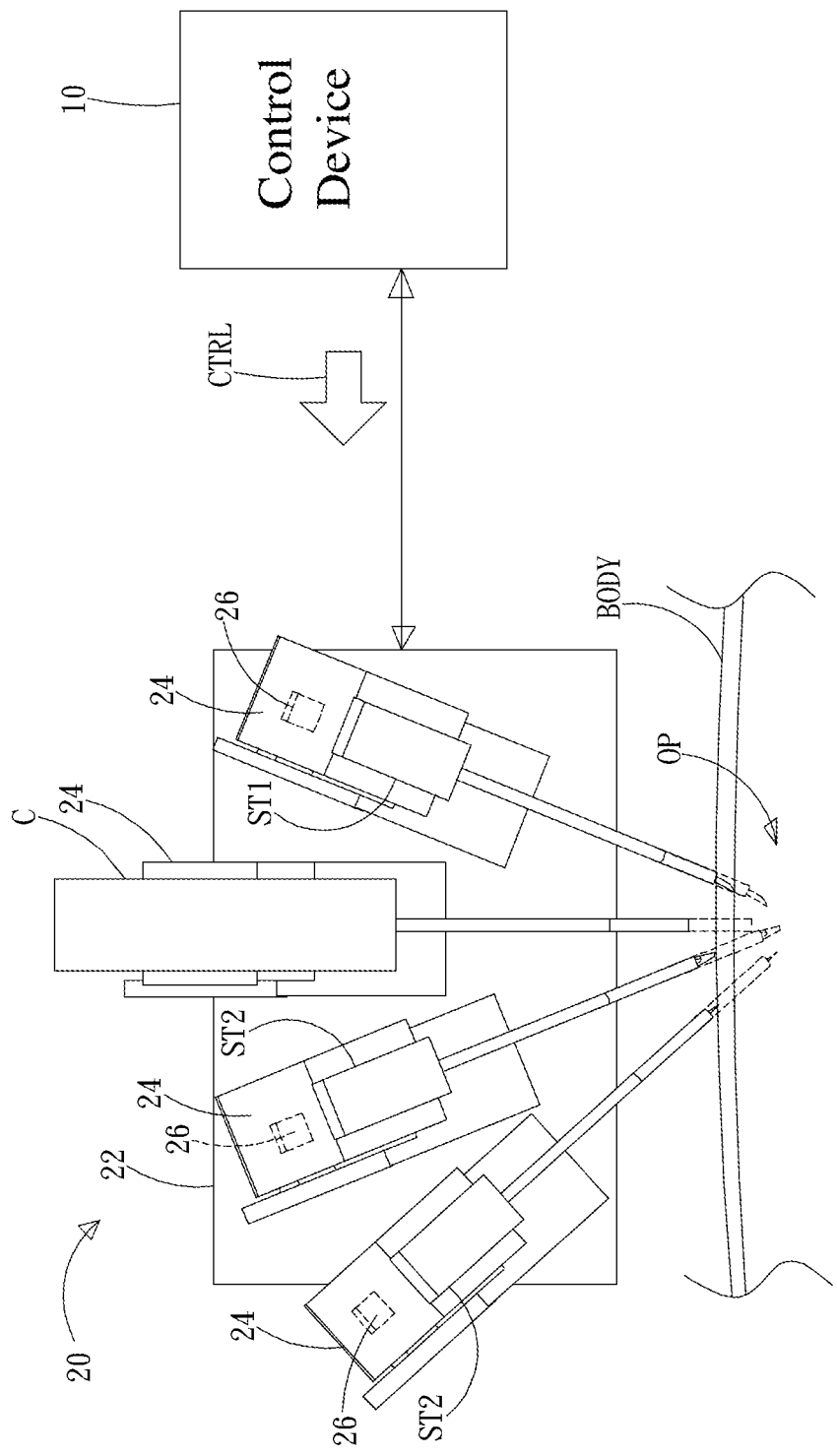
FIG. 2A-2E: Schematic diagram of devices in an embodiment of this application.
Figure 2B:
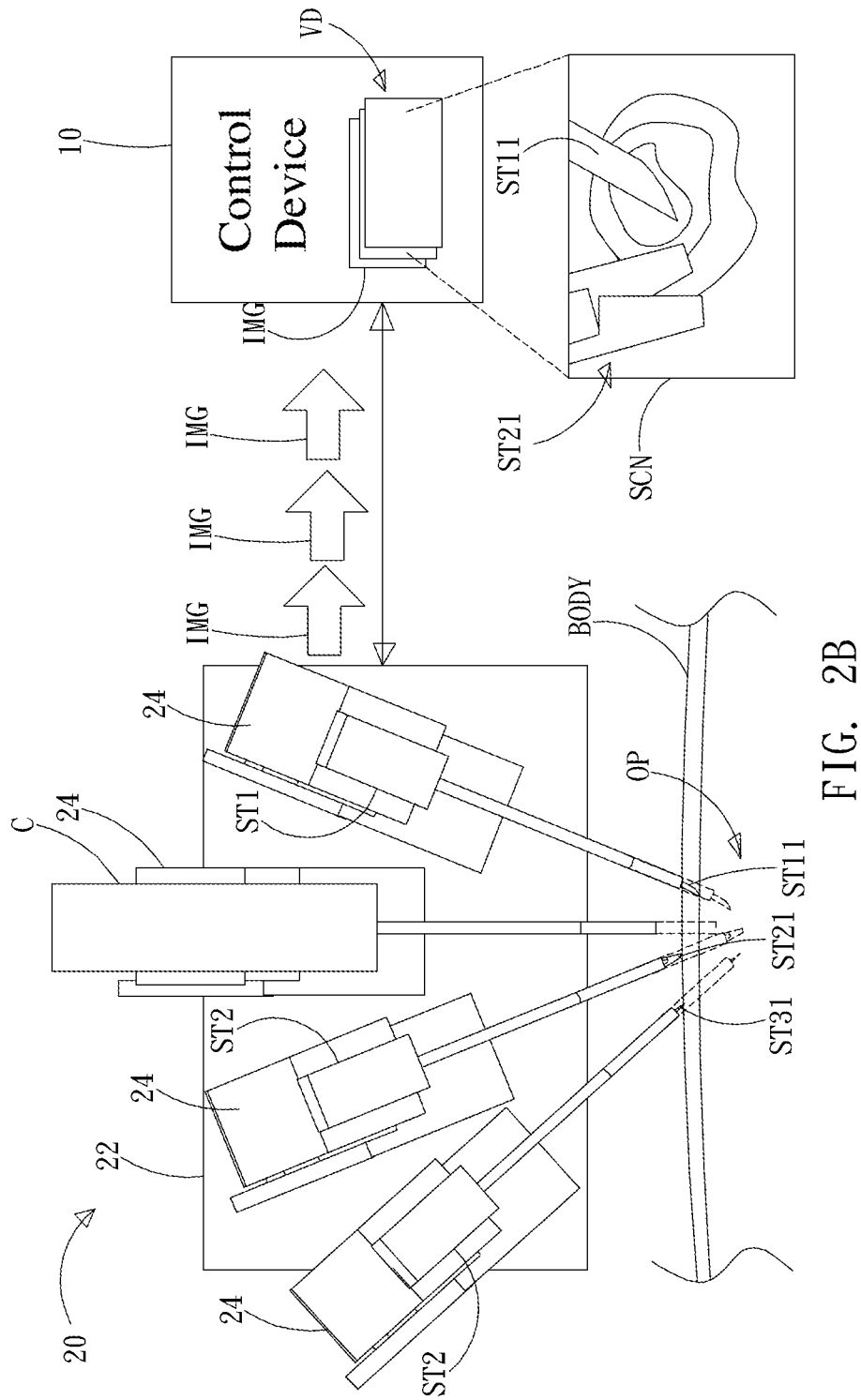

As shown in FIG. 2A, in step S10, the user controls the Operating Portion 24 of the Remote Surgical Device 20 to enter the human body via the Control Device 10 and perform a surgical operation such as the minimally invasive surgery for bile duct resection; that is, the Image Capturing Unit C, First Surgical Tool ST1, Second Surgical Tool ST2 and Third Surgical Tool ST3 being connected with the Operating Portion 24 come into the human body. In the subsequent step S20 (as shown in FIG. 2B), through the control of the Control Device 10, it uses the Image Capturing Unit C of the Remote Surgical Device 20 to capture a plurality of operation images IMG corresponding to the surgical operation to the Control Device 10 and forms the video data VD; the corresponded display screen SCN, which is the display screen of surgical operation OP; the display screen SCN displays the Mini Scalpel ST11 and the Jig ST21.

Figure 2C:
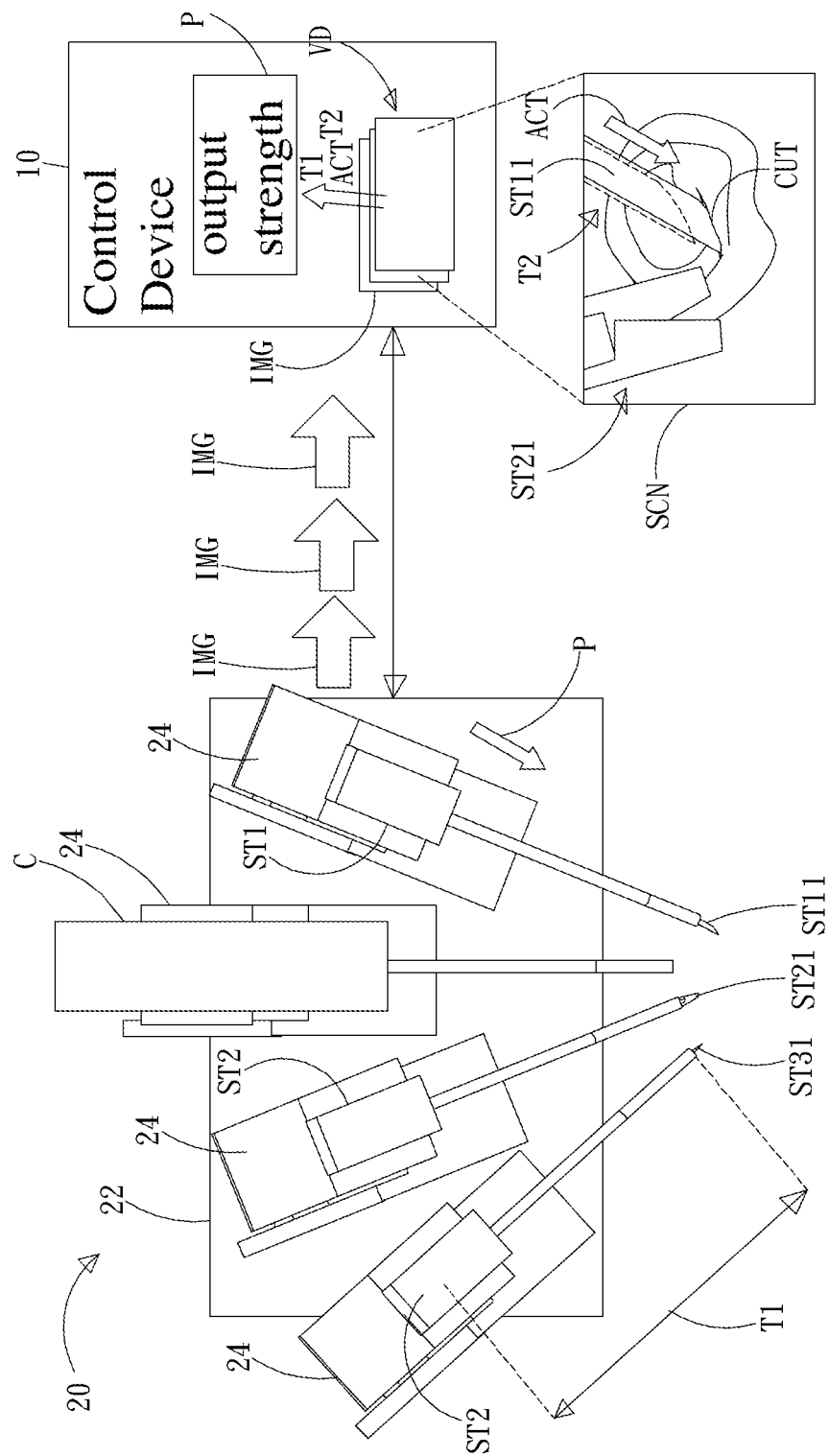

As shown in FIG. 2C, In step S30, the Control Device 10 follows the operation images IMG in the video data VD said above to obtain a First torque component T1 formed in the operation images IMG of the Operation Portion 24; in this embodiment, we use the First torque component T1 corresponding to an element action ACT formed by the element connected with the Operation Portion 24, that is, the CUT made the cutting action of the Mini Scalpel ST11, as a demonstrating example; yet, yet, it isn't limited to this arrangement in this application; it also can use the clamping action of the Jig ST21 or the drilling action of the Drill ST31 or the actions of other surgical operation tools.

Figure 2D:
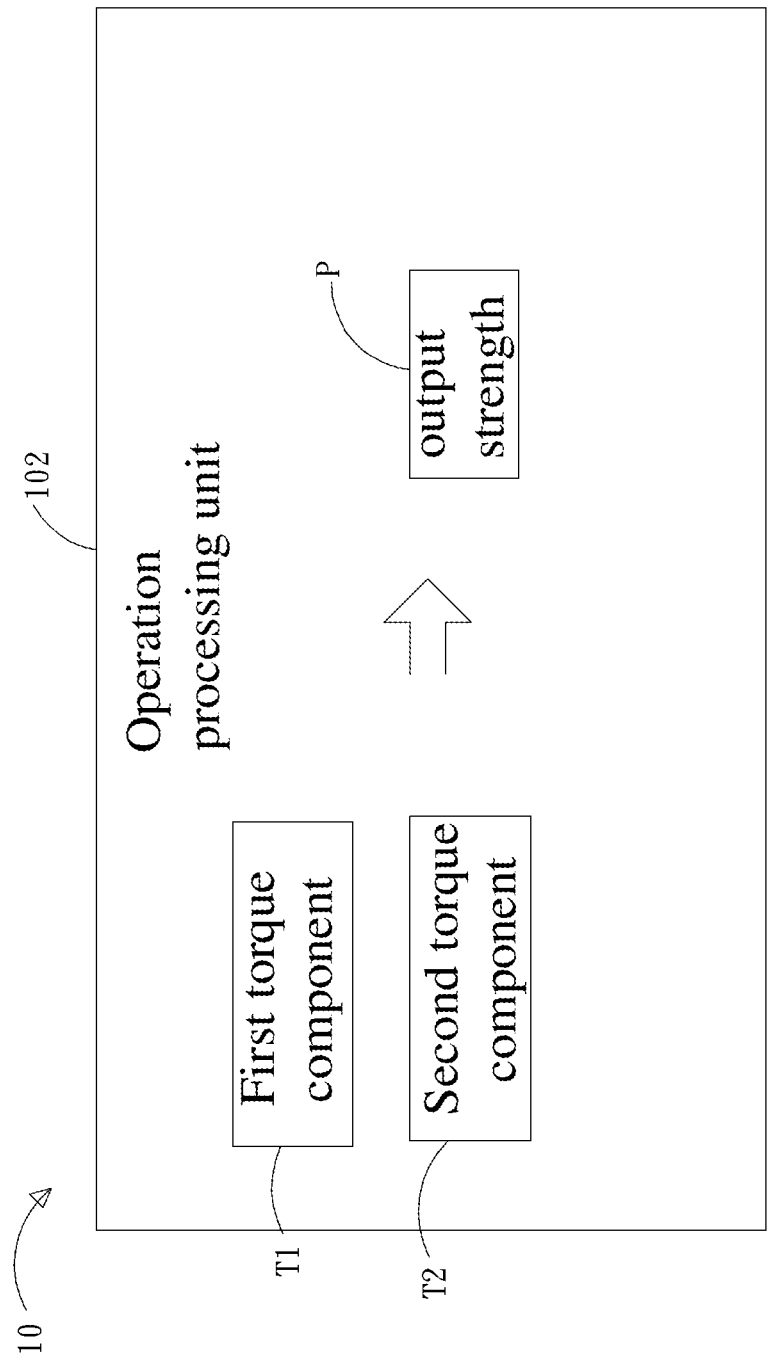
Figure 2E:
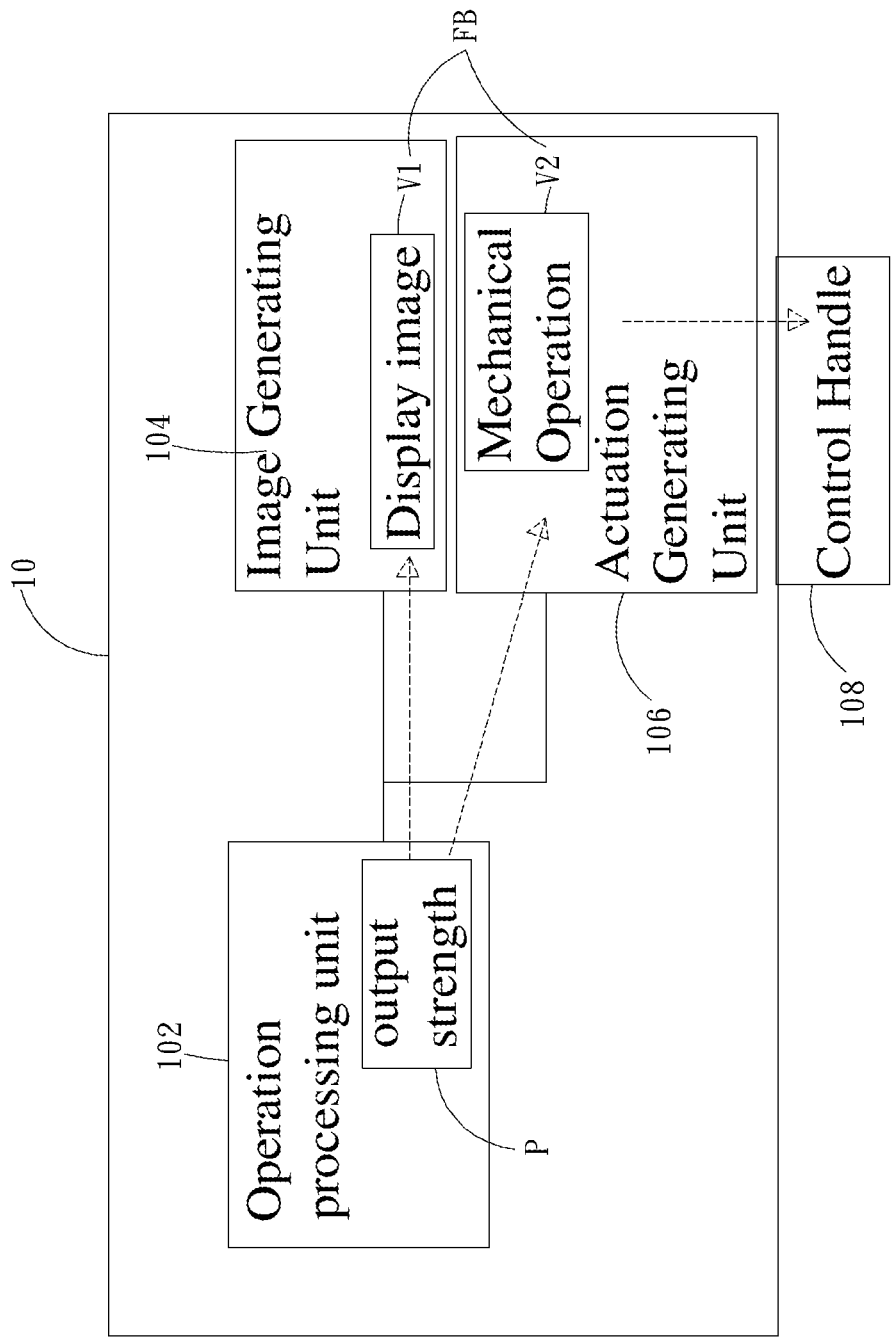

Following the above, in step S40, as shown in FIG. 2C and FIG. 2D, the Control Device 10 obtains one of the mechanical forces from the Remote Surgical Device 20 to the Operation Portion 24 through the Operation processing unit 102 according to the pre-set data. The Second torque component T2 is combined with the First torque component T1 obtained in step S30 to operate the output strength P of the Remote Surgical Device 20 output to the Operation Portion 24. Then, in step S50, as shown in FIG. 2E, the Operation processing unit 102 of the Control Device 10 performs step S30. The data corresponding to the obtained output strength P is transmitted to an Image Generating Unit 104 or an Actuation Generating Unit 106, and a force feedback FB is generated correspondingly, in particular, a corresponding Display image V1 or a Mechanical Operation V2 is generated according to the output strength P; for example, the display screen SCN transmits a force numerical image or a feedback thrust to the Control Handle 108 of the Control Device 10.

Therefore, this application uses the operation images IMG obtained by the Image Capturing Unit C of the Remote Surgical Device 20 to obtain the output strength P through image processing and operation; and then converts the output strength P into the corresponding force feedback FB. Therefore, the operator who operates the Control Device 10 can easily obtain the output state of the Remote Surgical Device 20, and thereby avoiding the operator from applying excessive force when operating the Remote Surgical Device 20, and thus avoiding surgical accidents.

Figure 3:
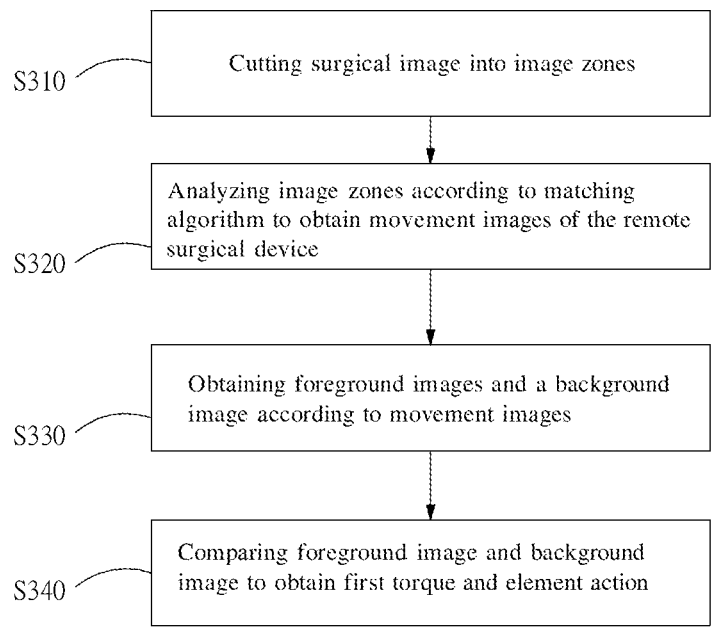
FIG. 3: Flowchart of the control device following the images to operate the first torque component in this application.

In addition, refer to FIG. 3, which is a flow chart that the control device in this application follows the image to operate the first torque component. As shown in the figure, the flow of the control device operating the first torque component in the above step S30 of this application is as follows:

Step S310: Cutting surgical image into image zones;

Step S320: Analyzing image zones according to matching algorithm to obtain movement images of remote surgical device;

Step S330: Obtaining foreground images and a background image according to movement images; and Step S340: Comparing foreground image and background image to obtain first torque component and element action.

Figure 4A:
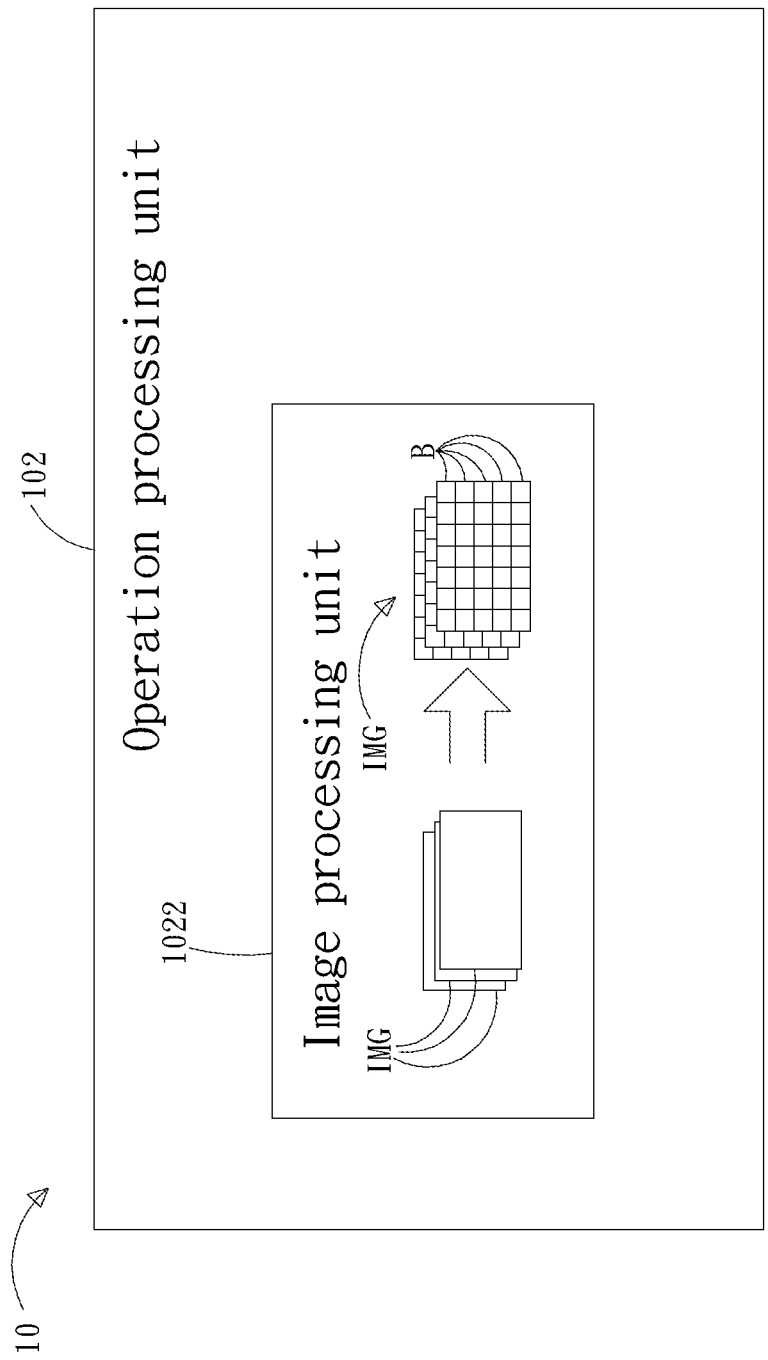
FIG. 4A-4D: Schematic diagram of image algorithm in an embodiment of this application.
Figure 4B:
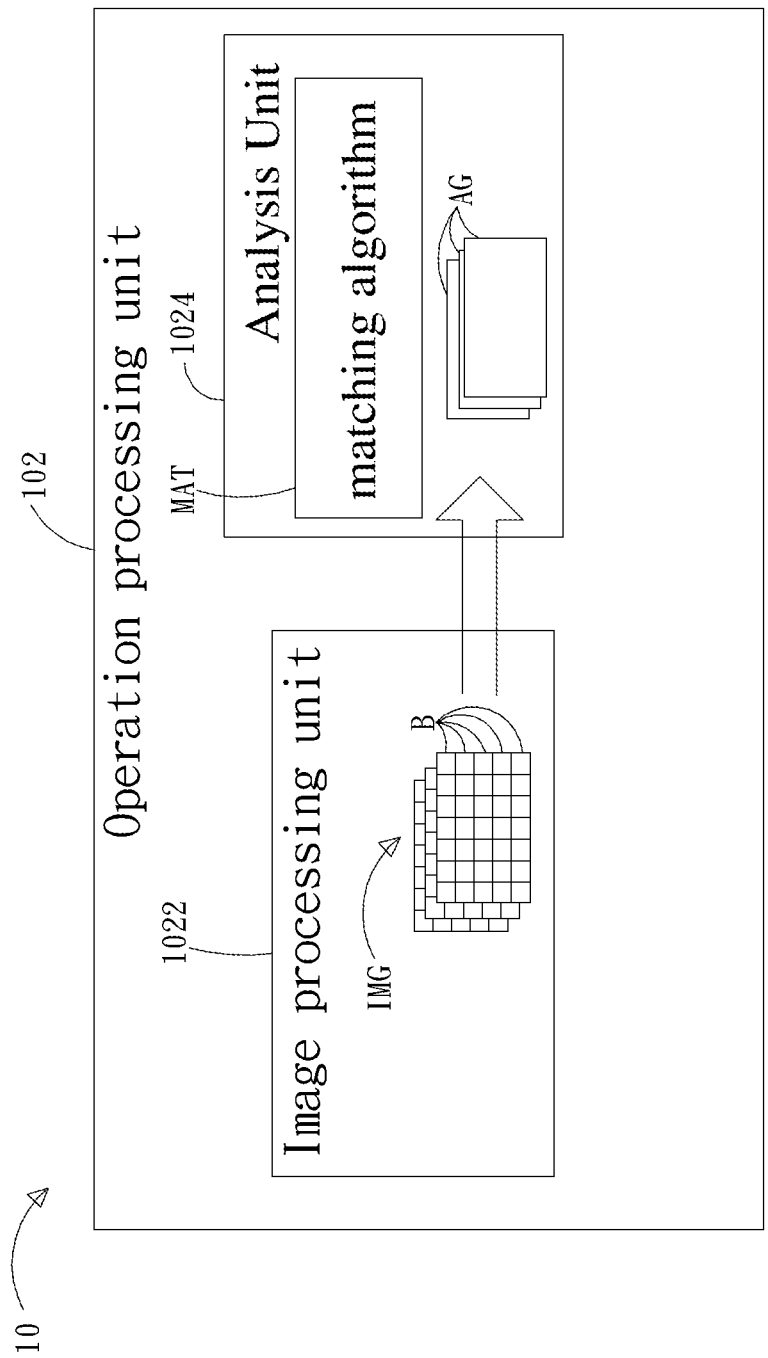

In step S310, as shown in FIG. 4A, the Operation processing unit 102 of the Control Device 10 has an Image Operation processing unit 1022 to cut the received operation images IMG into a plurality of image zones B; and then in step S320, the Analysis Unit 1024 of the Operation processing unit 102 in this application operates a matching algorithm MAT for analysis, and extracts the corresponding movement images AG from the operation images IMG. The matching algorithm operated by the Operation processing unit 102 is the Full search, Three-step search, Diamond search, Sum of absolute difference (SAD), Mean absolute error (MAE) or Mean squared error (MSE). In addition, the Analysis Unit 1024 can further label the movement images to distinguish different element actions.

Figure 4C:
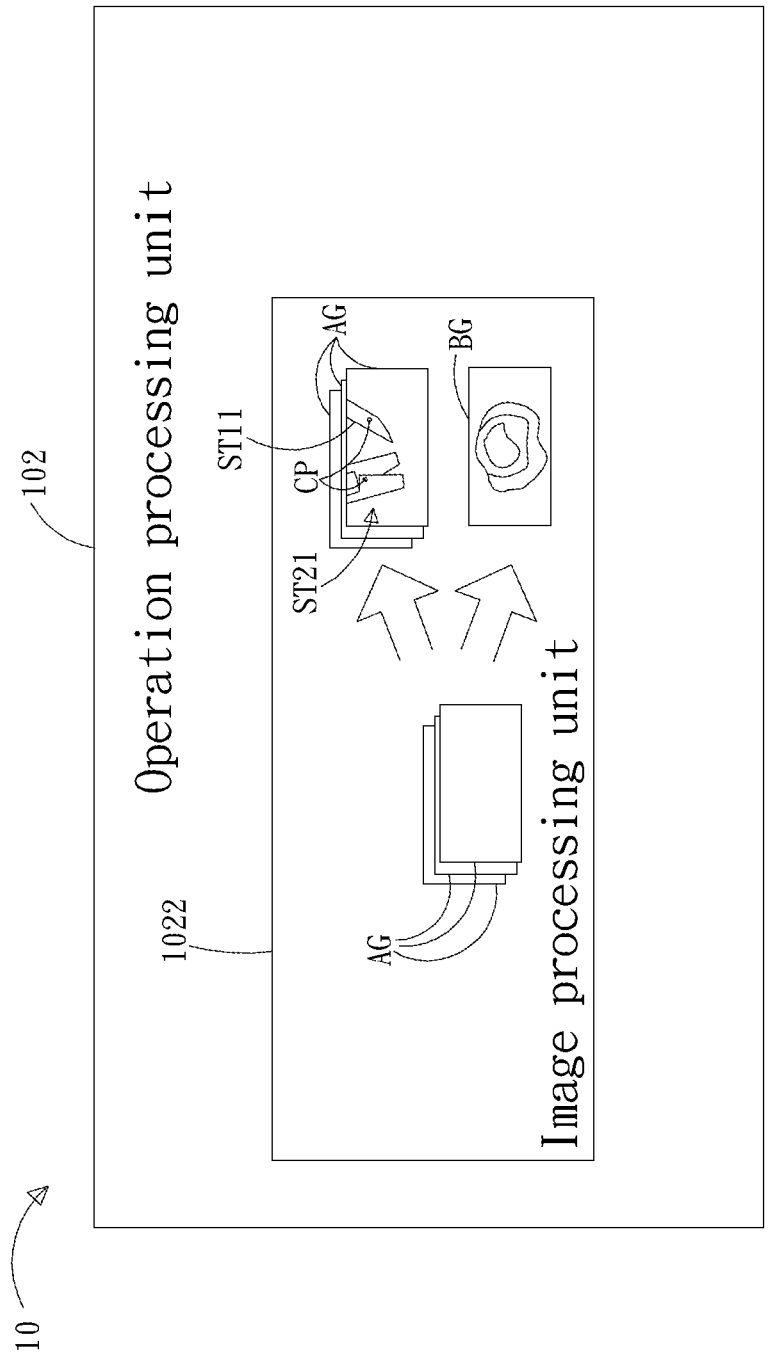
Figure 4D:
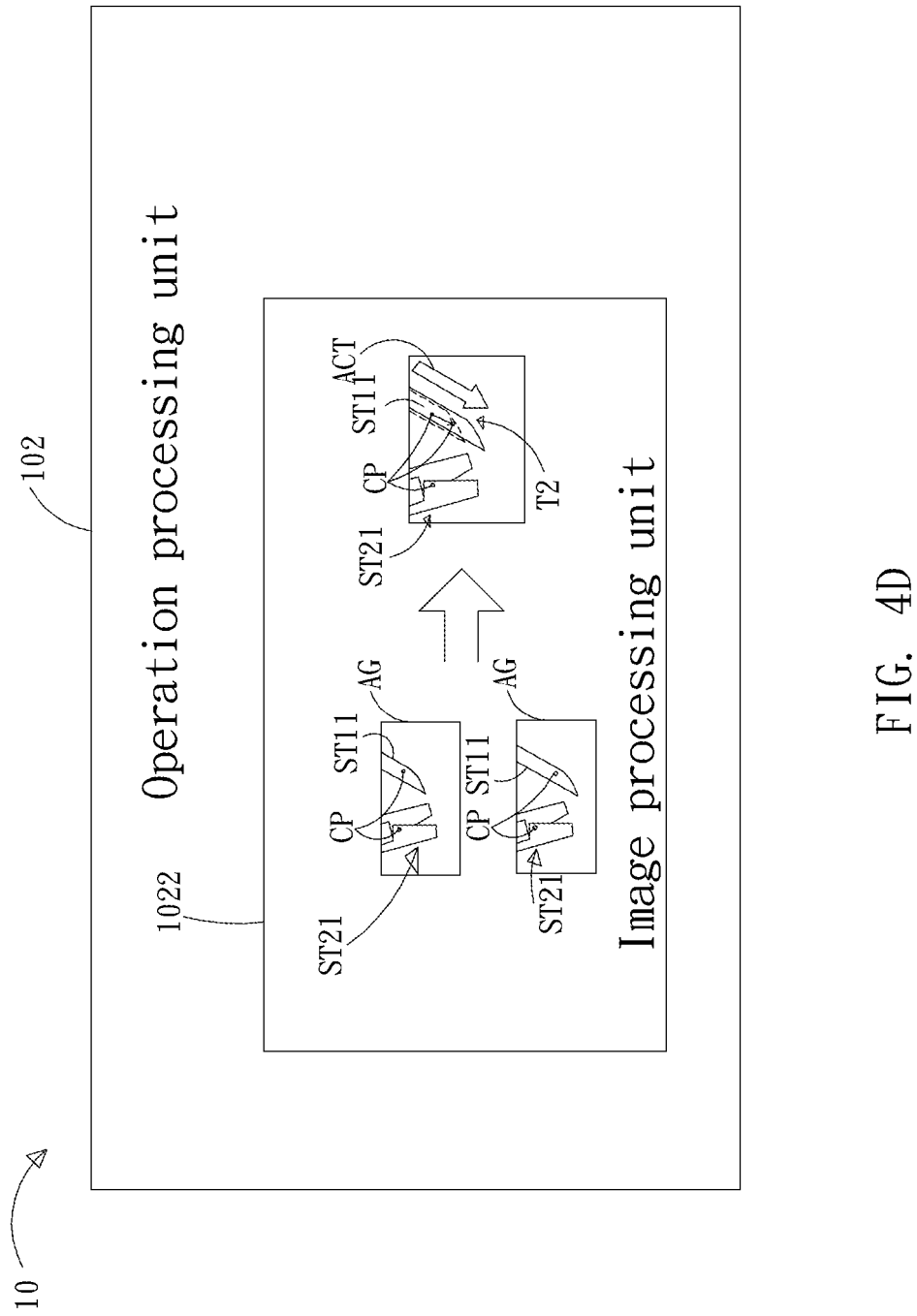

Following the above, in step S330, as shown in FIG. 4C, the Image Operation processing unit 1022 extracts the foreground images FG and the background images BG from the movement images AG obtained in step S320, where the foreground images FG are the moving images of the movement images AG and the background image BG is a static image among multiple movement images AG and is in a fixed scene. Generally speaking, the foreground images FG will appear more, while the background images BG are relatively less. In step S340, the foreground images are compared with the background image to obtain the First torque component T1 corresponding to element action ACT (as shown in FIG. 2C). In this embodiment, the image Operation processing unit 1022 is used to obtain the foreground images. As for an example, the multiple Element Center Points CP of the images FG are used to obtain an output vector VEC based on the Element Center Points CP, and the first torque component T1 corresponding to the element action ACT (as shown in FIG. 2C) is obtained by the output vector VEC; yet, this application is not limited to this, the element action ACT can be tracked by capturing the contour of the element to further obtain the First torque component T1, or the foreground images FG can be further used for dynamic tracking to further obtain the First torque component T1 and the element action ACT.

What is claimed is:

1. A method for generating a force feedback from a remote surgical device, including steps of:
    using an image capturing unit of a remote surgical device to capture a plurality of surgical images corresponding to a surgical operation being transmitted to a control device;
    obtaining a first torque component of an operating portion according to the surgical images by the control device;
    operating an output strength of the remote surgical device according to the first torque component and a second torque component from the remote surgical device to the operating portion, by the control device; and
    generating a force feedback according to the output strength by the control device.

2. The method for generating force feedback from the remote surgical device of claim 1, wherein in the step of using an image capturing unit of a remote surgical device to capture a plurality of surgical images corresponding to a surgical operation and send them to a control device, a pressure sensor is further used to sense a pressure taken by the operating portion.

3. The method for generating force feedback from the remote surgical device of claim 2, wherein in the step of operating an output strength of the remote surgical device according to the first torque component and the second torque component from the remote surgical device to the operating portion in the step, the control device further operates the output strength according to the bearing pressure.

4. The method for generating force feedback from the remote surgical device of claim 1, wherein the operating portion is connected with a jig, a drill, a file, a scraper, a saw, a screwdriver, or a surgical tool for repairing or removing part of the tissue by drilling, grinding, cutting or scraping, the operating portion is provided with a pressure sensor, a piezoelectric sensor, an elastic sensor, an optical camera, a laser scanner or an ultrasonic scanner.

5. The method for generating force feedback from the remote surgical device of claim 1, wherein in the step of the control device obtaining a first torque component of the operating portion according to the surgical images, the method further including the steps of:
    cutting the surgical images to a plurality of image zones respectively;
    analyzing the image zones according to a matching algorithm to obtain a plurality of movement images of the remote surgical device;
    obtaining a plurality of foreground images and at least one background image according to the movement images; and
    comparing the foreground images with the background image and obtaining the first torque component.

6. The method for generating force feedback from the remote surgical device of claim 5, wherein in the step of obtaining a plurality of movement images of the remote surgical device, the movement images are further labeled.

7. The method for generating force feedback from the remote surgical device of claim 5, wherein in the step of comparing the foreground images with the background image, a force vector is obtained according to the center points of the plurality of elements of the foreground images and used to obtain the first torque component.

8. The method for generating force feedback from the remote surgical device of claim 5, wherein in the step of comparing the foreground images with the background image, a color of the background image is further obtained and compared with a color coefficient table to adjust the first torque component.

9. The method for generating force feedback from the remote surgical device of claim 5, wherein the matching algorithm is the Full search, Three-step search, Diamond Search, Sum of absolute difference (SAD), Mean absolute error (MAE) or Mean squared error (MSE).

10. The method for generating force feedback from the remote surgical device of claim 1, wherein in the step of generating a force feedback by the control device according to the output strength, the control device generates a displays images or a mechanical operation corresponding to the force feedback according to the output strength.

11. The method for generating force feedback from the remote surgical device of claim 10, wherein the displayed image is a numerical image of force strength, and the mechanical operation is a feedback thrust.

* * * * *